US010542779B2

(12) United States Patent
Zinovik et al.

(10) Patent No.: US 10,542,779 B2
(45) Date of Patent: Jan. 28, 2020

(54) AEROSOL-GENERATING DEVICE, SYSTEM AND METHOD WITH A HEATED GAS SENSOR

(71) Applicant: Philip Morris Products S.A., Neuchatel (CH)

(72) Inventors: Ihar Nikolaevich Zinovik, Peseux (CH); Jerome Courbat, Colombier (CH)

(73) Assignee: Philip Morris Products S.A., Neuchatel (CH)

( * ) Notice: Subject to any disclaimer, the term of this patent is extended or adjusted under 35 U.S.C. 154(b) by 97 days.

(21) Appl. No.: 15/578,902

(22) PCT Filed: Jun. 29, 2016

(86) PCT No.: PCT/EP2016/065205
§ 371 (c)(1),
(2) Date: Dec. 1, 2017

(87) PCT Pub. No.: WO2017/001520
PCT Pub. Date: Jan. 5, 2017

(65) Prior Publication Data
US 2018/0168223 A1 Jun. 21, 2018

(30) Foreign Application Priority Data
Jun. 30, 2015 (EP) .................................... 15174501

(51) Int. Cl.
A24F 13/00 (2006.01)
A24F 47/00 (2006.01)
(Continued)

(52) U.S. Cl.
CPC ....... *A24F 47/008* (2013.01); *G01N 27/4065* (2013.01); *G01N 27/4074* (2013.01); *H05B 3/44* (2013.01)

(58) Field of Classification Search
CPC ...................................................... A24F 47/00
(Continued)

(56) References Cited

U.S. PATENT DOCUMENTS 9,635,886 B2 *   5/2017   Tu .......................... A24F 47/008
2014/0209105 A1   7/2014   Sears et al.
(Continued)

FOREIGN PATENT DOCUMENTS

WO   WO 2013/060784 A2   5/2013
WO   WO 2013/098397 A2   7/2013
WO   WO 2016/062786 A1   4/2016

OTHER PUBLICATIONS

International Search Report and Written Opinion dated Sep. 5, 2016 in PCT/EP2016/065205, filed Jun. 29, 2016.
(Continued)

*Primary Examiner* — Phuong K Dinh
(74) *Attorney, Agent, or Firm* — Oblon, McClelland, Maier & Neustadt, L.L.P.

(57) ABSTRACT

There is provided an aerosol-generating device configured to heat an aerosol-forming substrate, including: a power supply; a heater positioned to heat the aerosol-forming substrate to form an aerosol; a controller configured to control a supply of power from the power supply to the heater; and a gas sensor that is sensitive to a particular gas or gases, a response of the gas sensor being dependent on a temperature of the gas sensor, and the controller being connected to the gas sensor and being configured to monitor signals from the gas sensor.

16 Claims, 7 Drawing Sheets

(51) Int. Cl.
*G01N 27/406* (2006.01)
*G01N 27/407* (2006.01)
*H05B 3/44* (2006.01)

(58) Field of Classification Search
USPC .................................................. 131/329, 328
See application file for complete search history.

(56) References Cited

U.S. PATENT DOCUMENTS

| | | |
|---|---|---|
| 2014/0321837 A1 | 10/2014 | Flick |
| 2014/0378790 A1 | 12/2014 | Cohen |
| 2015/0068541 A1 | 3/2015 | Sears et al. |
| 2015/0230521 A1 | 8/2015 | Talon |
| 2016/0337141 A1* | 11/2016 | Cameron ............... H04L 12/185 |
| 2017/0303597 A1* | 10/2017 | Tsui ..................... H05B 1/0297 |

OTHER PUBLICATIONS

European Office Action dated Oct. 4, 2019 in corresponding European Patent Application No. 16734317.17, (4 pages).

\* cited by examiner

AEROSOL-GENERATING DEVICE, SYSTEM AND METHOD WITH A HEATED GAS SENSOR

The invention relates to aerosol-generating devices and systems which operate by heating an aerosol-forming substrate. In particular the invention relates to aerosol generating devices and systems in which it is desirable to maintain the temperature of the aerosol-forming substrate within a temperature range in order to ensure the production of a desirable aerosol. Electrically heated smoking devices are examples of this type of device.

One potential problem with electrically heated smoking devices, whether they are configured to heat a liquid aerosol-forming substrate or a solid aerosol-forming substrate such as a cigarette, is that if the temperature of the aerosol-forming substrate gets too high then combustion of the aerosol-forming substrate can occur. This can lead to the generation of compounds within the generated aerosol that taste unpleasant and are generally undesirable.

This problem is particularly acute in systems in which the user can insert their own aerosol-forming substrate into the device. Different aerosol-forming substrates behave differently when heated. In particular the temperature at which combustion occurs will vary depending on the composition of the substrate and its moisture content. Accordingly a device that simply maintains the temperature of a heater within a predetermined temperature range may not produce desirable aerosol for all the different substrates that might be used with it.

It is an object of the present invention to provide an aerosol generating device and system that can detect operating conditions associated with an undesirable substrate or with substrate combustion, but that is efficient to operate, compact and inexpensive.

In a first aspect there is provided an aerosol-generating device configured to heat an aerosol-forming substrate, comprising:

a power supply;

a heater positioned to heat the aerosol-forming substrate to form an aerosol;

a controller configured to control the supply of power from the power supply to the heater; and a gas sensor that is sensitive to a particular gas or gases, wherein a response of the gas sensor is dependent on a temperature of the gas sensor, and wherein the controller is connected to the gas sensor and is configured to monitor signals from the gas sensor.

By using a gas sensor that is sensitive to a particular gas or gases, such as oxidizing and reducing gases, and that has a response that is dependent on the temperature, a variety of different operating conditions can be detected.

The gas sensor is advantageously configured to operate within an operational temperature range above ambient temperature. The gas sensor may be positioned such that the heater heats the gas sensor to within its operational temperature range when heating the aerosol-forming substrate to form an aerosol.

The gas sensor may be a semiconductor gas sensor. In particular, the gas sensor may be a metal-oxide gas sensor. In one example, the gas sensor is a N-type semiconductor gas sensor, and in particular a tin-oxide gas sensor. N-type semiconductor sensors decrease in electrical resistance in the presence of a reducing gas, such as carbon monoxide (CO) or ammonia, and increase in electrical resistance in the presence of oxidizing gas, such as oxygen, nitric oxide (NO), or nitrogen dioxide ($NO_2$). A P-type semiconductor gas sensor can also be used. P-type semiconductor gas sensors behave in the opposite manner, so they increase in electrical resistance in the presence of a reducing gas and decrease in electrical resistance in the presence of oxidizing gas.

The gas sensor may be configured to operate between 200° C. and 400° C. This is the typical operating range of an N-type or P-type semiconductor gas sensor. Semiconductor gas sensors operate by virtue of a chemical reaction that takes place when the gas comes in direct contact with the sensor. At temperatures between 200° C. and 400° C. the sensor is more sensitive because the chemical reaction rate is increased and is more effective.

The controller may be configured to monitor an electrical resistance or change of electrical resistance of the sensor. The electrical resistance or change of electrical resistance of the sensor is indicative of the presence of a reducing or oxidising gas.

The gas sensor may be provided with an integrated gas sensor heater. This is a feature of some commercially available semiconductor gas sensors. The gas sensor heater may be used in the aerosol-generating device to heat the gas sensor in addition to, or as an alternative to, the heater positioned to heat the aerosol-forming substrate.

The device may comprise a plurality of gas sensors, at least two of the gas sensors configured to be sensitive to different gases. So one sensor may be configured to detect reducing gases and another may be configured to detect oxidising gases. Alternatively, both gas sensors may be sensitive to reducing gases but may be differently tuned (by changing the composition, fabrication or doping of the gas sensing layer) to be particularly sensitive to different gases. For example, one gas sensor may be tuned to sense CO while another may be tuned to be sensitive to $NO_2$.

The heater may comprise a heating element formed from an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum, platinum, gold and silver. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese-, gold- and iron-containing alloys, and super-alloys based on nickel, iron, cobalt, stainless steel, Timetal® and iron-manganese-aluminium based alloys. In composite materials, the electrically resistive material may optionally be embedded in, encapsulated or coated with an insulating material or vice-versa, depending on the kinetics of energy transfer and the external physicochemical properties required.

The heater may comprise an internal heating element or an external heating element, or both internal and external heating elements, where "internal" and "external" refer to the aerosol-forming substrate. An internal heating element may take any suitable form. For example, an internal heating element may take the form of a heating blade. Alternatively, the internal heater may take the form of a casing or substrate having different electro-conductive portions, or an electrically resistive metallic tube. Other alternatives include a heating wire or filament, for example a Ni—Cr (Nickel-Chromium), platinum, tungsten or alloy wire or a heating plate.

An external heating element may take any suitable form. For example, an external heating element may take the form of one or more flexible heating foils on a dielectric substrate, such as polyimide. The flexible heating foils can be shaped to conform to the perimeter of the substrate receiving cavity. Alternatively, an external heating element may take the form of a metallic grid or grids, a flexible printed circuit board, a moulded interconnect device (MID), ceramic heater, flexible carbon fibre heater or may be formed using a coating technique, such as plasma vapour deposition, on a suitable shaped substrate. An external heating element may also be formed using a metal having a defined relationship between temperature and resistivity. In such an exemplary device, the metal may be formed as a track between two layers of suitable insulating materials. An external heating element formed in this manner may be used to both heat and monitor the temperature of the external heating element during operation.

The heater advantageously heats the aerosol-forming substrate by means of conduction. The heater may be at least partially in contact with the substrate, or the carrier on which the substrate is deposited. Alternatively, the heat from either an internal or external heating element may be conducted to the substrate by means of a heat conductive element.

The heater may be deposited in or on a supporting substrate. In one such embodiment, the heater is an electrically resistive heating element formed using a metal, such as platinum, having a defined relationship between temperature and resistivity. In such an exemplary device, the metal may be formed as a track on a suitable insulating substrate material, such as ceramic material, and then sandwiched in another insulating material, such as a glass. Heaters formed in this manner may be used to both heat and monitor the temperature of the heating elements during operation.

When the heater is mounted on a supporting substrate and the gas sensor may advantageously be mounted on the supporting substrate, proximate to the heater. In this way the heater can be used to heat the gas sensor to its optimal operating temperature without requiring separate heating of the gas sensor, or at least requiring less dedicated heating of the gas sensor. This is an efficient use of power, which is a significant advantage in a handheld, battery operated device.

The supporting substrate may be configured for insertion into the aerosol-forming substrate. For example, the supporting substrate may be in the form of a blade, with the heater deposited on one or both sides of the blade.

The gas sensor may be positioned on the supporting substrate overlying the heater. This ensures that the gas sensor receives sufficient heat from the heater. Alternatively, or in addition, a gas sensor may positioned on an opposite face of the substrate to the heater. This provides a lower but a more uniform temperature at the gas sensor. Alternatively, a gas sensor and the heater may be positioned in a single layer on one surface of the substrate. This may reduce the number of fabrication steps required and so may save cost.

In a second aspect of the invention, there is provided an aerosol-generating device configured to heat an aerosol-forming substrate, comprising:
    a power supply;
    a supporting substrate;
    a heater positioned on the supporting substrate to heat the aerosol-forming substrate to form an aerosol;
    a semiconductor gas sensor positioned on the supporting substrate; and
    a controller configured to control the supply of power from the power supply to the heater;
    wherein the controller is connected to the gas sensor and is configured to monitor signals from the gas sensor.

Features of the device of the first aspect may be applied to the device of the second aspect of the invention. In particular, it should be clear that the gas sensor may be a semiconductor gas sensor, such as a metal oxide gas sensor. The heater may be as described with reference to the first aspect of the invention, advantageously being an electrically resistive heating element formed using a metal, such as platinum.

As used herein, an 'aerosol-generating device' relates to a device that interacts with an aerosol-forming substrate to generate an aerosol. The aerosol-forming substrate may be part of an aerosol-generating article, for example part of a smoking article. An aerosol-generating device may be a smoking device that interacts with an aerosol-forming substrate of an aerosol-generating article to generate an aerosol that is directly inhalable into a user's lungs thorough the user's mouth.

As used herein, the term 'aerosol-forming substrate' relates to a substrate capable of releasing volatile compounds that can form an aerosol. Such volatile compounds may be released by heating the aerosol-forming substrate. An aerosol-forming substrate may conveniently be part of an aerosol-generating article or smoking article.

As used herein, the terms 'aerosol-generating article' and 'smoking article' refer to an article comprising an aerosol-forming substrate that is capable of releasing volatile compounds that can form an aerosol. For example, an aerosol-generating article may be a smoking article that generates an aerosol that is directly inhalable into a user's lungs through the user's mouth. An aerosol-generating article may be disposable. A smoking article may be, or may comprise, a tobacco stick.

The device according to the first aspect or the second aspect of the invention may be an electrically operated device and in particular may be an electrically heated smoking device.

In both the first and second aspects of the invention, the controller may be configured to stop or reduce the supply of power to the heater based on the signals from the gas sensor. The signals from the gas sensor may be indicative of a fault condition, such as a substrate being heated that has already been used or that is inappropriate for the device. In those circumstances, power to the heater may be stopped. In both the first and second aspects of the invention, the controller may be configured to the compare signals from the gas sensor with data stored in memory to determine a fault condition.

By monitoring a level of particular gases generated based on signals from the gas sensor, the controller has information about the composition of the aerosol being generated without needing to know anything about the aerosol-forming substrate being used. The gas sensor may be, for example, tuned to detect carbon monoxide (CO) or nitric oxide ($NO_x$). Carbon monoxide is an established indicator of combustion and in particular of incomplete combustion. For example, in a burning cigarette heavier molecular weight volatile compounds are "cracked" into smaller molecules, such as low molecular weight hydrocarbons, carbon monoxide and carbon dioxide. Incomplete combustion can occur because during use, particularly between user puffs, insufficient oxygen is transported to the burning cigarette for complete combustion. Nitric oxide is often produced during combustion too. Nitric oxide includes both nitric oxide (NO) and nitrogen dioxide (NO2) but is often abbreviated to $NO_x$. In burning biomass $NO_x$ typically results from fuel bound nitrogen. For example plant based substrates, such as tobacco based substrates contain significant amount of nitrates. The gas sensor may also be configured to detect other gases, such as gases containing a carboxyl group or carboxyl groups, or aldehydes, which may be undesirably generated in electronic cigarettes using a liquid substrate, as a result of combustion of constituents of the liquid substrate.

In both the first and second aspects of the invention, the controller may be configured to reduce the supply of power to the heater when the level of reducing or oxidising gas exceeds a first threshold gas level. As used herein the term "level of gases" may refer to a concentration of gases within an airflow or an absolute amount of gases detected. The level of gases may be determined by a difference in the electrical resistance of the gas sensor from an expected electrical resistance. Preferably, the controller is configured to reduce power to the heater to a level that has the effect of reducing the temperature of the heater or aerosol-forming substrate.

Alternatively, or in addition, the device may comprise an indicator, and the controller may be configured to activate the indicator when a fault is determined. The controller may activate the indicator when the level of oxidising or reducing gas exceeds a second threshold level. The indicator may be a visual indicator on the device such as a light emitting diode (LED) or an audible indicator, such as a speaker. The user may then choose to discontinue using the device until the indicator is deactivated. The first threshold level may be the same as or different to the second threshold level.

In both the first and second aspects of the invention, the controller may be configured to stop the supply of power to the heater from the power source when the reducing gas or oxidising gas level reaches a stop level. The controller may be configured to monitor the level of reducing or oxidising gas after the controller has stopped the supply of power to the heater and may be configured to activate an indicator if the reducing or oxidising gas level remains above the stop level. This indicator can be audio or visual. This allows for the detection of self-perpetuating combustion within the substrate. If the heat generated by the combustion is sufficient to cause further generation of the reducing or oxidising gas, without additional heat from the heater, then the user is alerted and can choose to remove the substrate from the device.

In both the first and second aspects of the invention, the controller may be configured to regulate the supply of power to the heater from the power supply to maintain the level of sensed gas below the first threshold level. A feedback loop may be used so that the controller continuously adjusts the power supplied to the heater dependent on the level of gas detected. By reducing power to the heater, the level of the particular gas generated can be reduced. The amount of power reduction may be a predetermined amount or may be a reduction that is controlled based on a sensed temperature.

In both the first and second aspects of the invention, the device may comprise an air inlet and an air outlet, and, in use, the aerosol-forming substrate may be positioned in an air flow path between air inlet and the air outlet. Air is drawn in through the air inlet, past or through the aerosol-forming substrate to the air outlet. In a smoking system, the user puffs on the air outlet to draw air and generated aerosol (smoke) into their mouth.

The gas sensor may be positioned to detect gases drawn into the device through the air inlet, herein referred to as sidestream gas. In a smoking system, this allows the detection of combustion gases within "sidestream" smoke, which is not directly inhaled by the user.

Alternatively, the gas sensor may be positioned to detect gases adjacent to or downstream of the aerosol-forming substrate, herein referred to as mainstream combustion gas. In a smoking system, this allows the detection of gases within "mainstream" smoke, which is directly inhaled by the user.

The threshold levels of gas used for determining whether to reduce or stop the supply of power to the heater, and to determine whether to activate an indicator, depend on whether the gas sensor is positioned to detect sidestream combustion gas or mainstream combustion gas.

In both the first and second aspects of the invention, the power supply may be any suitable power supply, for example a DC voltage source. In one embodiment, the power supply is a Lithium-ion battery. Alternatively, the power supply may be a Nickel-metal hydride battery, a Nickel cadmium battery, or a Lithium based battery, for example a Lithium-Cobalt, a Lithium-Iron-Phosphate, Lithium Titanate or a Lithium-Polymer battery.

In both the first and second aspects of the invention, the controller may comprise a microcontroller. The microcontroller may include a PID regulator for controlling the power supplied to the heater. The controller may be configured to supply power to the heater as pulses of electrical power. The controller may be configured to alter the supply of power to the heater by altering the duty cycle of the pulses of power.

In both the first and second aspects of the invention, the aerosol generating device may comprise a housing. Preferably, the housing is elongate. The structure of the housing, including the surface area available for condensation to form, will affect the aerosol properties and whether there is liquid leakage from the device. The housing may comprise a shell and a mouthpiece. In that case, all the components may be contained in either the shell or the mouthpiece. The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

In both the first and second aspects of the invention, preferably the aerosol generating device is portable. The aerosol generating device may be a smoking device and may have a size comparable to a conventional cigar or cigarette. The smoking device may have a total length between approximately 30 mm and approximately 150 mm. The smoking device may have an external diameter between approximately 5 mm and approximately 30 mm.

In a third aspect, there is provided an aerosol generating system comprising an aerosol-generating device according to the first or second aspect and an aerosol-forming substrate received in or coupled to the device.

In the first, second and third aspects of the invention, during operation, the aerosol-forming substrate may be completely contained within the aerosol-generating device. In that case, a user may puff on a mouthpiece of the aerosol-generating device.

Alternatively, during operation a smoking article containing the aerosol-forming substrate may be partially contained within the aerosol-generating device. In that case, the user may puff directly on the smoking article. The heating element may be positioned within a cavity in the device, wherein the cavity is configured to receive an aerosol-forming substrate such that in use the heating element is within the aerosol-forming substrate.

The smoking article may be substantially cylindrical in shape. The smoking article may be substantially elongate. The smoking article may have a length and a circumference substantially perpendicular to the length. The aerosol-forming substrate may be substantially cylindrical in shape. The aerosol-forming substrate may be substantially elongate. The aerosol-forming substrate may also have a length and a circumference substantially perpendicular to the length.

The smoking article may have a total length between approximately 30 mm and approximately 100 mm. The smoking article may have an external diameter between approximately 5 mm and approximately 12 mm. The smoking article may comprise a filter plug. The filter plug may be located at the downstream end of the smoking article. The filter plug may be a cellulose acetate filter plug. The filter plug is approximately 7 mm in length in one embodiment, but may have a length of between approximately 5 mm to approximately 10 mm.

In one embodiment, the smoking article has a total length of approximately 45 mm. The smoking article may have an external diameter of approximately 7.2 mm. Further, the aerosol-forming substrate may have a length of approximately 10 mm. Alternatively, the aerosol-forming substrate may have a length of approximately 12 mm. Further, the diameter of the aerosol-forming substrate may be between approximately 5 mm and approximately 12 mm. The smoking article may comprise an outer paper wrapper. Further, the smoking article may comprise a separation between the aerosol-forming substrate and the filter plug. The separation may be approximately 18 mm, but may be in the range of approximately 5 mm to approximately 25 mm. The separation is preferably filled in the smoking article by a heat exchanger that cools the aerosol as it passes through the smoking article from the substrate to the filter plug. The heat exchanger may be, for example, a polymer based filter, for example a crimped PLA material.

In both the first, second and third aspects of the invention, the aerosol-forming substrate may be a solid aerosol-forming substrate. Alternatively, the aerosol-forming substrate may comprise both solid and liquid components. The aerosol-forming substrate may comprise a tobacco-containing material containing volatile tobacco flavour compounds which are released from the substrate upon heating. Alternatively, the aerosol-forming substrate may comprise a non-tobacco material. The aerosol-forming substrate may further comprise an aerosol former. Examples of suitable aerosol formers are glycerine and propylene glycol.

If the aerosol-forming substrate is a solid aerosol-forming substrate, the solid aerosol-forming substrate may comprise, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco, cast leaf tobacco and expanded tobacco. The solid aerosol-forming substrate may be in loose form, or may be provided in a suitable container or cartridge. Optionally, the solid aerosol-forming substrate may contain additional tobacco or non-tobacco volatile flavour compounds, to be released upon heating of the substrate. The solid aerosol-forming substrate may also contain capsules that, for example, include the additional tobacco or non-tobacco volatile flavour compounds and such capsules may melt during heating of the solid aerosol-forming substrate.

As used herein, homogenised tobacco refers to material formed by agglomerating particulate tobacco. Homogenised tobacco may be in the form of a sheet. Homogenised tobacco material may have an aerosol-former content of greater than 5% on a dry weight basis. Homogenised tobacco material may alternatively have an aerosol former content of between 5% and 30% by weight on a dry weight basis. Sheets of homogenised tobacco material may be formed by agglomerating particulate tobacco obtained by grinding or otherwise comminuting one or both of tobacco leaf lamina and tobacco leaf stems. Alternatively, or in addition, sheets of homogenised tobacco material may comprise one or more of tobacco dust, tobacco fines and other particulate tobacco by-products formed during, for example, the treating, handling and shipping of tobacco. Sheets of homogenised tobacco material may comprise one or more intrinsic binders, that is tobacco endogenous binders, one or more extrinsic binders, that is tobacco exogenous binders, or a combination thereof to help agglomerate the particulate tobacco; alternatively, or in addition, sheets of homogenised tobacco material may comprise other additives including, but not limited to, tobacco and non-tobacco fibres, aerosol-formers, humectants, plasticisers, flavourants, fillers, aqueous and non-aqueous solvents and combinations thereof.

Optionally, the solid aerosol-forming substrate may be provided on or embedded in a thermally stable carrier. The carrier may take the form of powder, granules, pellets, shreds, spaghettis, strips or sheets. Alternatively, the carrier may be a tubular carrier having a thin layer of the solid substrate deposited on its inner surface, or on its outer surface, or on both its inner and outer surfaces. Such a tubular carrier may be formed of, for example, a paper, or paper like material, a non-woven carbon fibre mat, a low mass open mesh metallic screen, or a perforated metallic foil or any other thermally stable polymer matrix.

The solid aerosol-forming substrate may be deposited on the surface of the carrier in the form of, for example, a sheet, foam, gel or slurry. The solid aerosol-forming substrate may be deposited on the entire surface of the carrier, or alternatively, may be deposited in a pattern in order to provide a non-uniform flavour delivery during use.

Although reference is made to solid aerosol-forming substrates above, it will be clear to one of ordinary skill in the art that other forms of aerosol-forming substrate may be used with other embodiments. For example, the aerosol-forming substrate may be a liquid aerosol-forming substrate. The liquid aerosol-forming substrate may comprise an aerosol former. Examples of suitable aerosol formers are glycerine and propylene glycol. If a liquid aerosol-forming substrate is provided, the aerosol-generating device preferably comprises means for retaining the liquid. For example, the liquid aerosol-forming substrate may be retained in a container. Alternatively or in addition, the liquid aerosol-forming substrate may be absorbed into a porous carrier material. The porous carrier material may be made from any suitable absorbent plug or body, for example, a foamed metal or plastics material, polypropylene, terylene, nylon fibres or ceramic. The liquid aerosol-forming substrate may be retained in the porous carrier material prior to use of the aerosol-generating device or alternatively, the liquid aerosol-forming substrate material may be released into the porous carrier material during, or immediately prior to use. For example, the liquid aerosol-forming substrate may be provided in a capsule. The shell of the capsule preferably melts upon heating and releases the liquid aerosol-forming substrate into the porous carrier material. The capsule may optionally contain a solid in combination with the liquid.

Alternatively, the carrier may be a non-woven fabric or fibre bundle into which tobacco components have been incorporated. The non-woven fabric or fibre bundle may comprise, for example, carbon fibres, natural cellulose fibres, or cellulose derivative fibres.

It is possible for the heater and gas sensor to be provided in a heater assembly that is separable from the power supply and/or controller. It may be that the heater and gas sensor typically have a different useful lifetime to the power supply or controller and so require replacement at different intervals. So it may be desirable to sell a heater assembly as a separate item to the rest of the device. Accordingly, in a fourth aspect there is provided a heating assembly for an aerosol-generating system, configured to heat an aerosol-forming substrate, the heating assembly comprising:

a heater positioned to heat the aerosol-forming substrate to form an aerosol; and a gas sensor that is sensitive to a particular gas or gases, wherein a response of the gas sensor is dependent on a temperature of the gas sensor.

The heater assembly can be provided with or without the aerosol-generating substrate.

Although the disclosure has been described by reference to different aspects, it should be clear that features described in relation to one aspect of the disclosure may be applied to the other aspects of the disclosure. In particular, features of the heater positioned to heat the aerosol-forming substrate, features of the gas sensor and features of the aerosol-forming substrate described with reference to the first, second and third aspects of the invention can be applied to the heater assembly of the fourth aspect of the invention.

The invention will be further described, by way of example only, with reference to the accompanying drawings, in which:

FIG. 2b is a schematic side view of the heater assembly of FIG. 2a;

Figure 1:
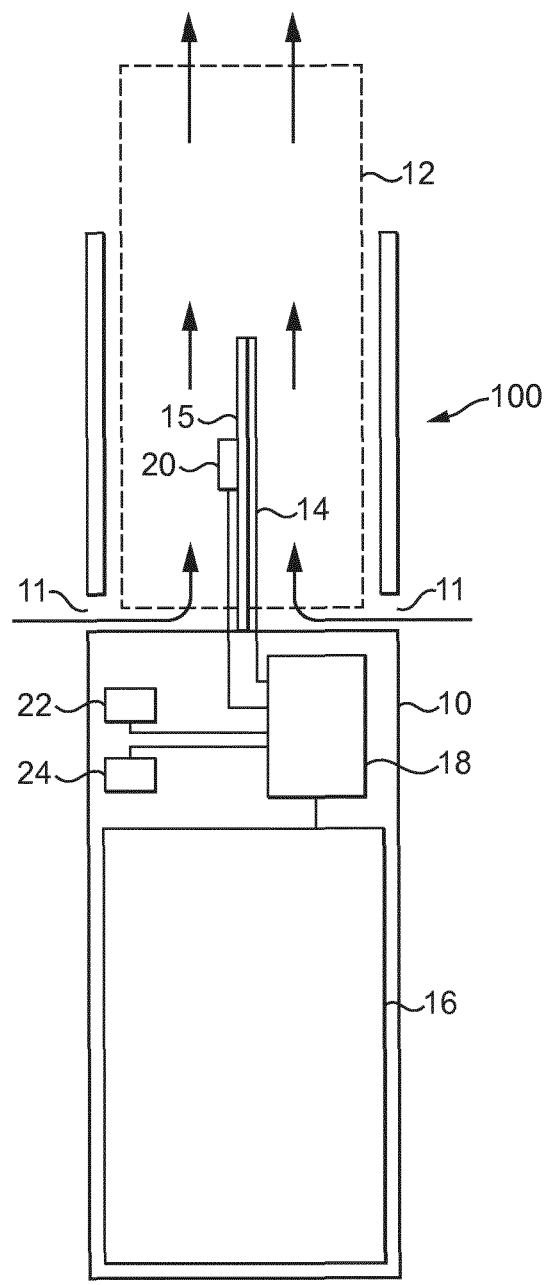
FIG. 1 is a schematic illustration of a first electrically heated smoking device in accordance with the invention.

In FIG. 1, the components of an embodiment of an electrically heated aerosol-generating device 100 are shown in a simplified manner. Particularly, the elements of the electrically heated aerosol-generating device 100 are not drawn to scale in FIG. 1. Elements that are not relevant for the understanding of this embodiment have been omitted to simplify FIG. 1.

The electrically heated aerosol-generating device 100 comprises a housing 10 and an aerosol-forming substrate 12, for example a cigarette. The aerosol-forming substrate 12 is pushed inside the housing 10 to come into thermal proximity with the heater 14. The aerosol-forming substrate 12 will release a range of volatile compounds at different temperatures. By controlling the operation temperature of the electrically heated aerosol-generating device 100 to be below the release temperature of some of the volatile compounds, the release or formation of these smoke constituents can be avoided.

Within the housing 10 there is an electrical power supply 16, for example a rechargeable lithium ion battery. A controller 18 is connected to the heater 14 on a heater support 15 and the electrical power supply 16. The controller 18 controls the power supplied to the heater 14 in order to regulate its temperature. Typically the aerosol-forming substrate is heated to a temperature of between 250 and 450 degrees centigrade.

The housing 10 includes air inlets 11 at the base of the cavity in the housing that receives the aerosol-forming substrate 12. In use, a user puffs on the cigarette and draws air through the air inlets 11, through the substrate 12 past the heater 14, and into their mouth.

In the described embodiment, the heater 14 is an electrically resistive track or tracks deposited on the heater support 15, which is a ceramic substrate. The ceramic substrate is in the form of a blade and is inserted into the aerosol-forming substrate 12 in use.

The controller 18 is also connected to a gas sensor 20, in this example a tin-oxide gas sensor, fixed to the ceramic substrate. The controller is also connected to a visual indicator 22, which in this example is an LED, and an audio indicator 24, which in this example is a speaker configured to emit a warning sound, as will be described.

Figure 2A:
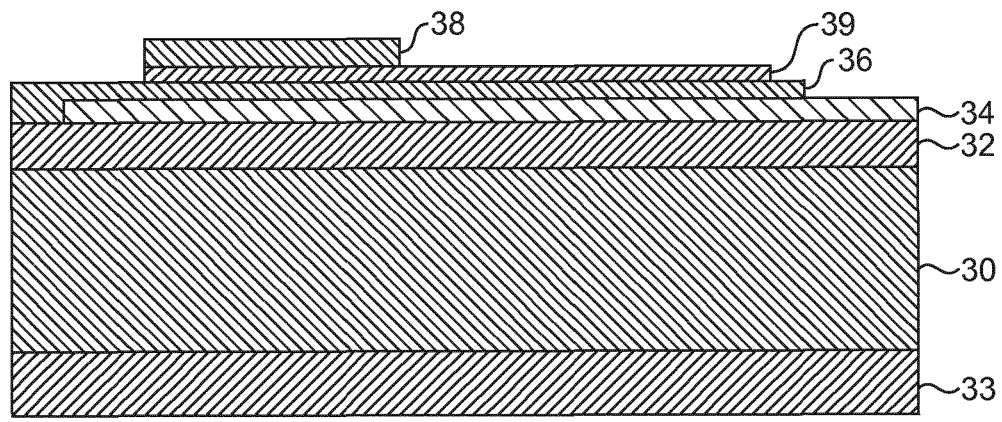
FIG. 2a is a schematic cross-sectional view of a heater assembly suitable for use in a device as shown in FIG. 1.

In the example shown in FIG. 1, the gas detector is positioned on the heater support 15 to detect gases within the aerosol-forming substrate FIG. 2a is a schematic cross-sectional view of a heater and gas sensor assembly suitable for use in a device as described with reference to FIG. 1. The heater support comprises a ceramic layer 30 on which two glass layers 32, 33 are deposited. The heater is a platinum track 34 on top of one of the glass layers 32. A further glass layer 36 is formed over the heater. The gas sensor 38 is a tin-oxide gas sensor. Electrodes 39 for carrying current to and from the gas sensor 38 are formed on the further glass layer 36 and the tin-oxide sensor deposited over the electrodes 39.

Figure 2B:
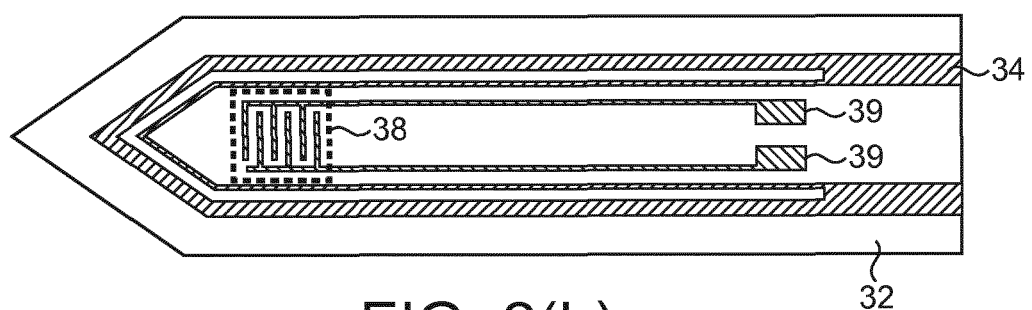

FIG. 2b is a side view of the heater and gas sensor assembly of FIG. 2a. It can be seen the electrodes 39 are formed under the tin-oxide sensor so that current has to pass through the tin oxide layer to pass from one electrode to the other. The platinum heater track passes around the gas sensor. Any suitable pattern may be used for the heater track. The example shown in FIG. 2b is illustrative of just one example.

In operation the heater 34 heats the ceramic substrate 30 and glass layers 32, 33, 36 as well as the gas sensor. They in turn heat the aerosol-forming substrate 12 received in the device. The optimal temperature for operation of the gas sensor matches the temperature required to form a desirable aerosol from the aerosol-forming substrate, so that no additional heating of the gas sensor is required.

Figure 3:
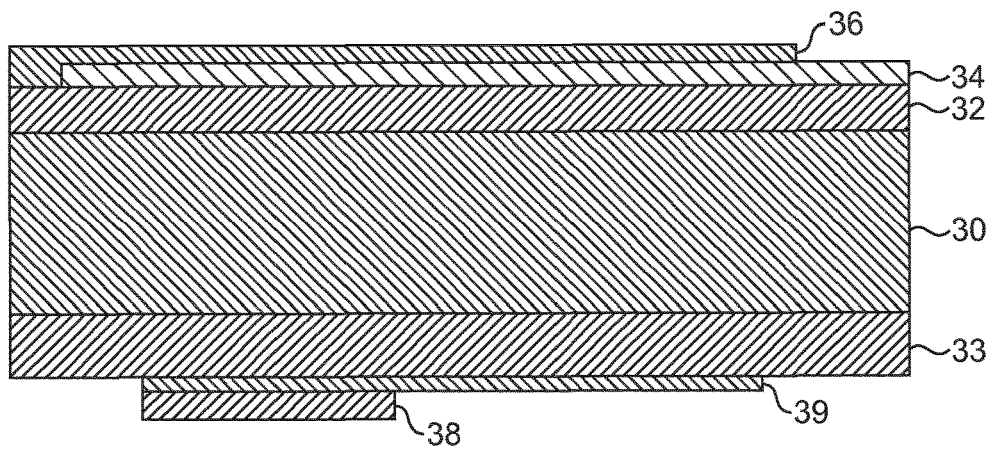
FIG. 3 is a schematic cross-sectional view of an alternative heater assembly suitable for use in a device as shown in FIG. 1.

Alternative configurations for the heater and gas sensor assembly in accordance with the invention are possible. FIG. 3 illustrates a first alternative, in which the gas sensor 38 and the electrodes 39 for the gas sensor are placed on the opposite face of the ceramic layer to the heater. Placing the gas sensor on the opposite face of the ceramic layer to the heater may be advantageous because in this position the gas sensor is heated to a slightly lower temperature and is more evenly heated than in the position shown in FIG. 2.

Figure 4:
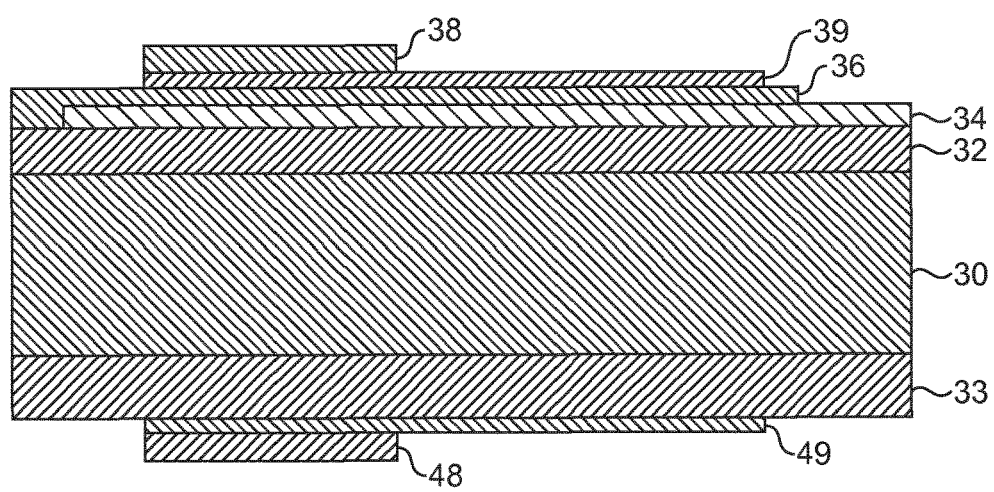
FIG. 4 is a schematic cross-sectional view of a further alternative heater assembly suitable for use in a device as shown in FIG. 1.

FIG. 4 illustrates a further alternative, in which two gas sensors are included. The first gas sensor 38 is positioned over the heater as in the embodiment of FIG. 2a. A second gas sensor 48, with associated electrodes 49, is placed on the opposite side of the ceramic layer to the heater, as in the embodiment of FIG. 3. Both gas sensors are connected to the controller 18. The first gas sensor 38 may be tuned to be sensitive to a different gas than the second gas sensor 48.

Figure 5:
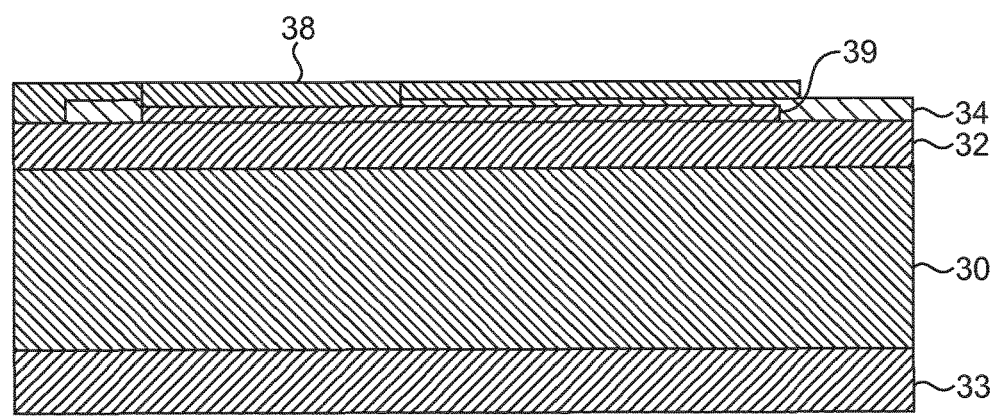
FIG. 5 is a schematic cross-sectional view of a still further alternative heater assembly suitable for use in a device as shown in FIG. 1.

FIG. 5 is a cross-sectional illustration of a further alternative in which the gas sensor 38 is positioned on the same glass layer 32 as the heater 34. The heater 34 extends around the gas sensor 38 so that the heater and the gas sensor 38 (and gas sensor electrodes 39) are electrically isolated from one another. The further glass layer 36, which covers and protect the heater 34 has an opening it, through which the gas sensor is exposed so that it can detect particular gases. Because this arrangement requires fewer deposition steps than the arrangement of FIG. 2a, it is less costly to manufacture.

In operation, when the device is activated by a user by pressing a button (not shown) on the device, the controller supplies power to the heater. The temperature of the heater rises as a result of Joule heating of the heater. The electrical resistance of the heater 14, 34 changes with temperature. The controller 18 is configured to monitor the electrical resistance of the heater 14 and to adjust the power supplied to the heater in order to maintain the temperature of the heater at a target temperature. The controller may also provide more sophisticated control to respond to changes in heat dissipation from the heater and in order to vary the target temperature over the course of a smoking session in response to other sensed parameters.

At the same time the controller 18 is configured to monitor the electrical resistance of the gas sensor 38 or gas sensors 38, 48.

Figure 6A:
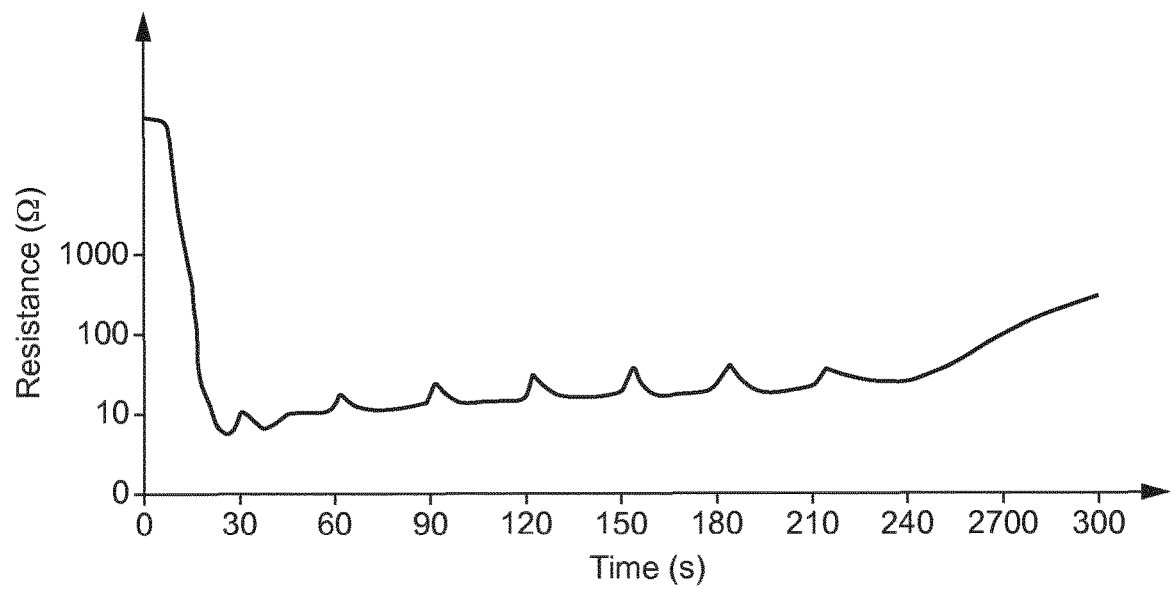
FIG. 6a illustrates the response of the gas sensor under normal operating conditions.

FIG. 6a is an illustration of the evolution of the electrical resistance of a tin-oxide gas sensor as shown in FIG. 2 during normal operation of the device with a suitable aerosol-forming substrate inserted. As the gas sensor 20 heats up during the first 20-30 seconds following activation of the heater, its electrical resistance falls. The temperature of the gas sensor is then held fairly constant during use. There is small increase in electrical resistance over the course of the smoking session, probably due to increased levels of oxidizing gases over the course of the smoking session as the aerosol-forming substrate dries out. Small spikes in electrical resistance occur during user puffs as the air flow past the gas sensor cools the gas sensor temporarily. If the device is configured to provide a variable temperature profile over the course of a smoking session, the controller 18 can normalise the electrical resistance of the gas sensor to account for that variable temperature.

The controller 18 includes a non-volatile memory that stores a normal electrical resistance profile for the gas sensor, as illustrated in FIG. 6a. This profile can be compared with actual measurements to determine if a fault condition exists.

Figure 6B:
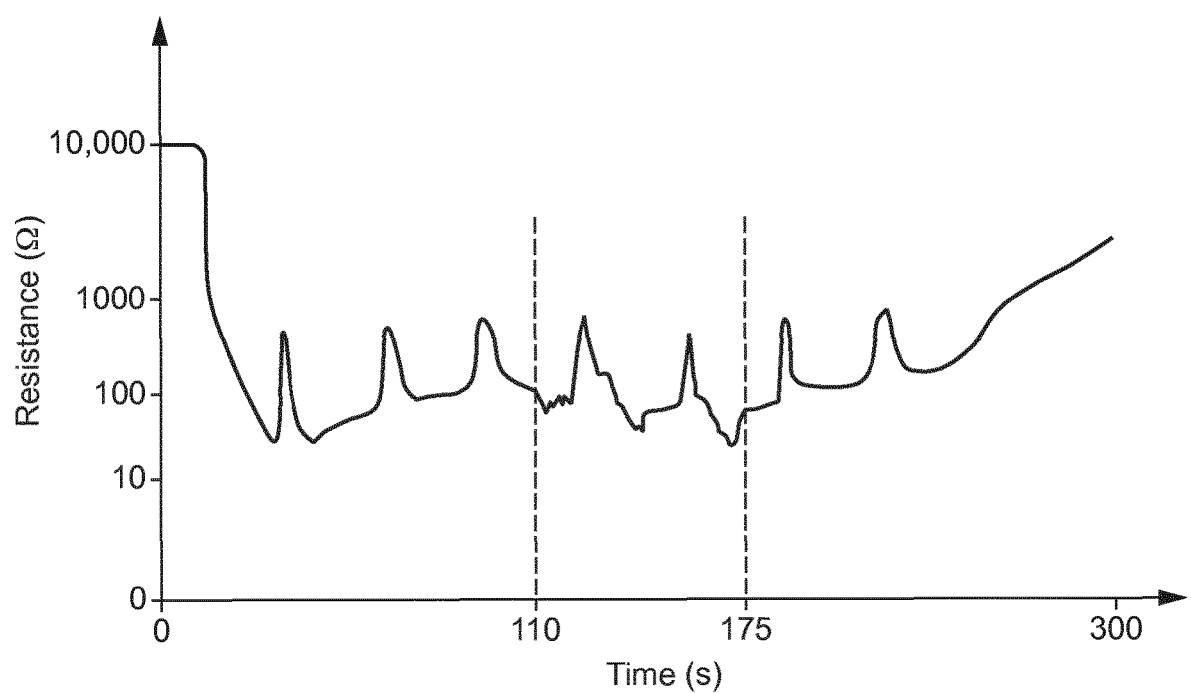
FIG. 6b illustrates the response of the gas sensor when exposed to combustion gases.

FIG. 6b illustrates the evolution of the electrical resistance of a tin-oxide gas sensor as shown in FIG. 2, in which the gas sensor 20 is exposed to reducing gases as a result of combustion of the aerosol-forming substrate 12. The gas sensor 20 is exposed to reducing gas, such as CO, between 110 seconds and 175 seconds after activation. It can be seen that the electrical resistance of the gas sensor drops when it is exposed to the reducing gas. By comparing a stored electrical resistance profile for normal operation, as shown in FIG. 6(a), with the measured resistance of the gas sensor, the controller can determine if something "abnormal" is occurring, and then abort the smoking session by preventing the supply of further power to the heater. The controller may be configured to diagnose a particular type of abnormal behaviour, or fault, based on the type of deviation from the expected electrical resistance profile, and may then take different actions or provide different indications to the user depending on the type of fault diagnosed. For example, the controller may be configured to reduce the temperature of the heater when low levels of reducing gas are sensed but may be configured to abort the smoking session if the level of reducing gas is sensed to be above a threshold. The controller may also be configured to provide different indications or alarm signals depending on the nature of the fault diagnosed.

Figure 6C:
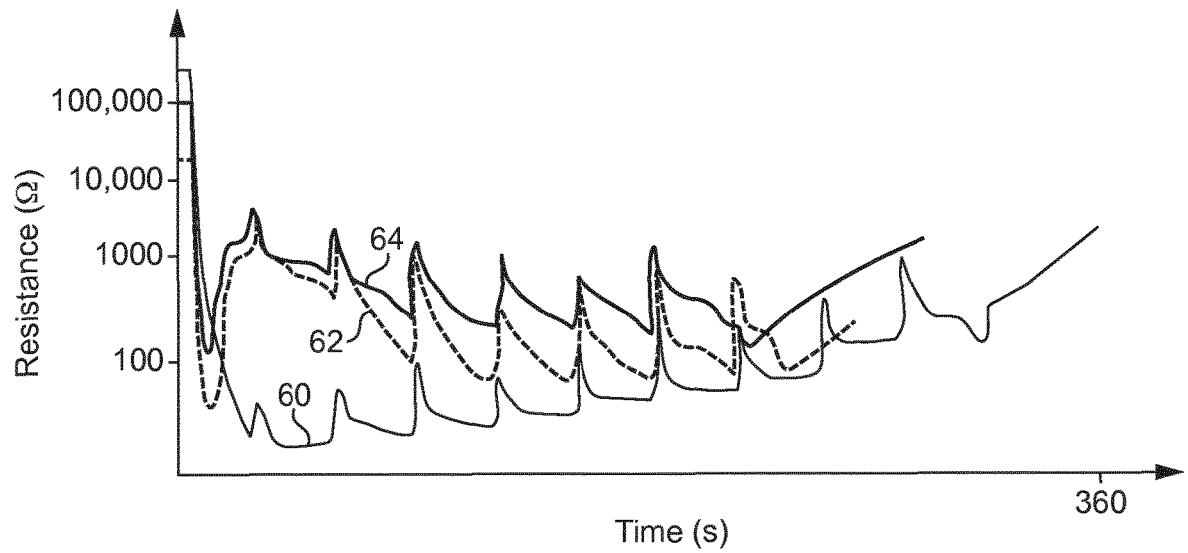
FIG. 6c illustrates the response of the gas sensor in the presence of an aerosol-forming substrate that has already been used.

Another type of fault is the use of a substrate that has already been used in a smoking session and so is depleted. FIG. 6c illustrates the response of the gas sensor in the presence of an aerosol-forming substrate that has already been used. Line 60 is the electrical resistance of the gas sensor during a first use of the aerosol-forming substrate. Line 62 is the electrical resistance of the gas sensor during a second use of the same substrate and line 64 is the electrical resistance of the gas sensor during a third use of the same substrate. It can be seen that during reuse of the same substrate the electrical resistance of the gas sensor is an order of magnitude higher in the first 30 seconds than during the first use. The aerosol-forming substrate becomes dry after the first use as the aerosol-former is exhausted. This leads to an increase in oxidizing gases initially. The controller may also be configured to control the temperature of the heater so that if heat dissipation from the heater is reduced, which occurs as the aerosol-forming substrate dries out, it reduces the temperature of the heater. This reduces the risk of combustion of the aerosol-forming substrate but may contribute to a higher resistance of the gas sensor. The initial higher electrical resistance of the gas sensor can be easily detected by the controller and the smoking session aborted. The resistance of the gas sensor thereafter tends to decrease during the smoking session with an already used substrate as the amount of reducing gases formed increases.

Figure 6D:
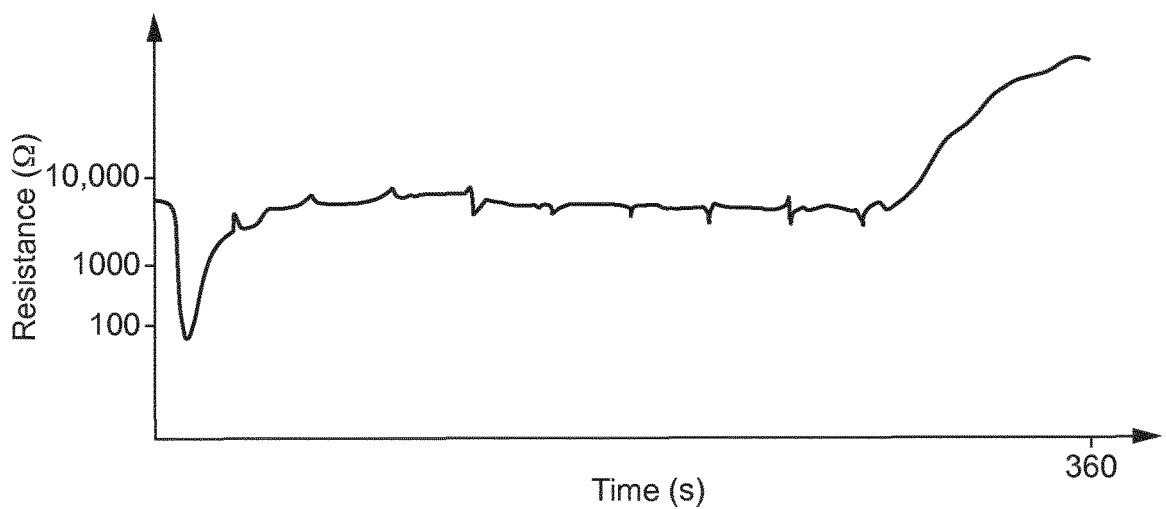
FIG. 6d illustrates the response of the gas sensor in the absence of an aerosol-forming substrate

FIG. 6d illustrates the response of the gas sensor in the absence of an aerosol-forming substrate. The electrical resistance of the gas sensor is an order of magnitude higher after first 30 seconds than in the presence of an appropriate aerosol-forming substrate. This is the result of a reduced temperature of the heater, as a result of the controller reducing power to the heater to lower the temperature of the heater when heat dissipation from the heater is reduced. There is also less significant cooling during user puffs.

Figure 6E:
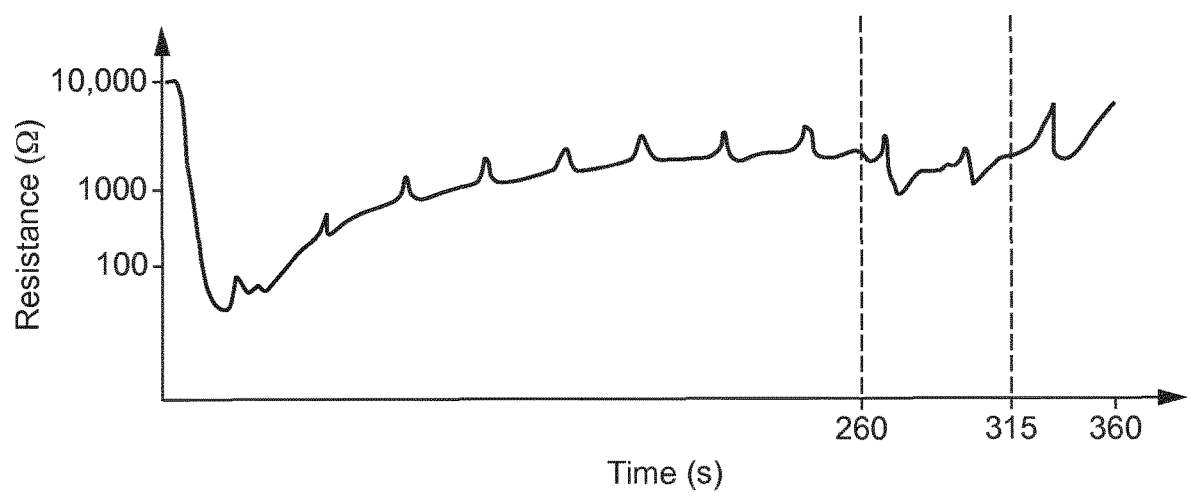
FIG. 6e illustrates the response of the gas sensor in the presence of an unsuitable aerosol-forming substrate.

FIG. 6e illustrates the response of the gas sensor in the presence of an unsuitable aerosol-forming substrate, in this example a substrate that has insufficient aerosol-former and so is too dry. The electrical resistance of the gas sensor is one or two orders of magnitude higher than in the presence of an appropriate aerosol-forming substrate. It can also be seen that between 260 and 310 seconds after activation there is significant reducing gas present, indicative of combustion of the aerosol-forming substrate.

The controller 18 can store in memory resistance profiles corresponding to each of these conditions and can correlate measured electrical resistance of the gas sensor with the stored profiles to diagnose a particular fault. The controller can then respond by stopping the smoking session or modifying the supply of power to the heater, as well as providing an indication of the fault to the user.

Figure 7:
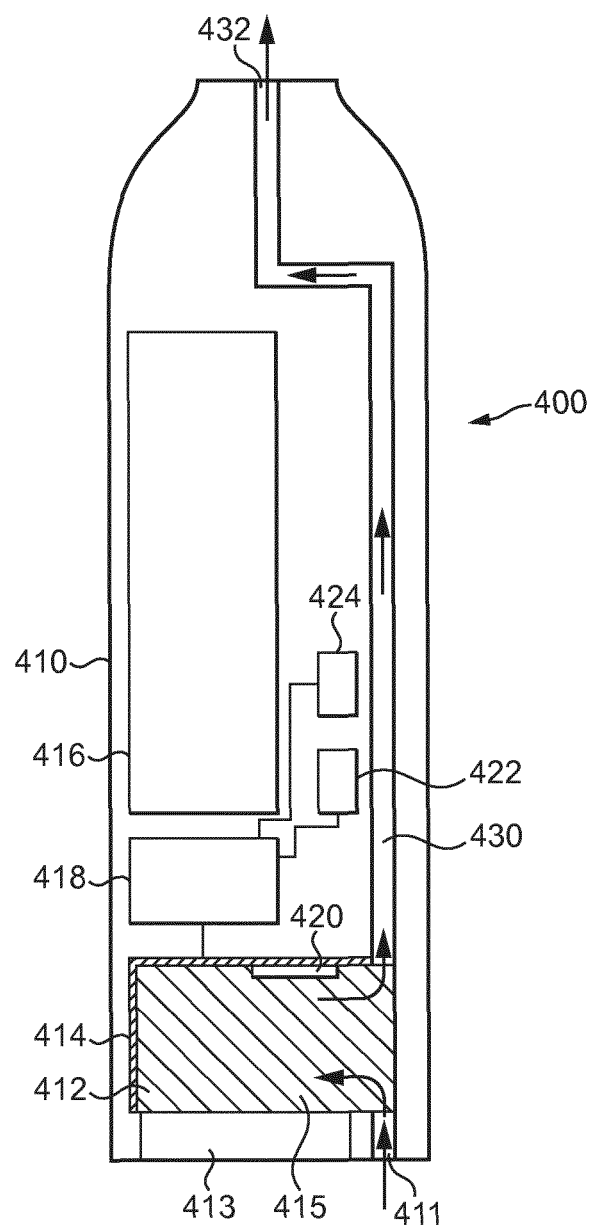
FIG. 7 is a schematic illustration of a second electrically heated smoking device in accordance with the invention.

FIG. 7 illustrates an alternative type of smoking system in accordance with the invention, which allows users to use loose tobacco or other substrates in the device. The device 400 comprises an oven chamber 415 in which loose tobacco 412 is loaded. The oven is heated by a flexible heater 414 lining the oven chamber 414. A controller 418 controls the supply of electrical power from a battery 410 to the heater 414. The controller is also connected to a gas sensor 420, an LED indicator 422 and an audio indicator 424, as described in the device of FIG. 1. Loose tobacco can be loaded into the oven by removing lid 413, loading an amount of tobacco into the oven chamber and then replacing the lid.

The device 400 has a mouthpiece 432 on which a user puffs to draw air and generated aerosol through the device. Air is drawn into the device through air inlet 411 into the oven chamber, past the gas sensor 420 and the air then flows through conduit 430 to the mouthpiece 432 and then into a user's mouth. Filter elements (not shown) can be provided in inlet 411 and at the entrance to conduit 430 to prevent tobacco blocking the airflow path.

Vapours from the heated aerosol-generating substrate are entrained in the airflow and drawn through the conduit. The vapours condense in the airflow to form an aerosol.

The gas sensor 420 is a metal oxide gas sensor and is mounted over the flexible heater 414, within the oven chamber 414, so it is directly heated by the heater to its operating temperature.

It should be clear that, the exemplary embodiments described above illustrate but are not limiting. In view of the above discussed exemplary embodiments, other embodiments consistent with the above exemplary embodiments will now be apparent to one of ordinary skill in the art.

The invention claimed is:

1. An aerosol-generating device configured to heat an aerosol-forming substrate, comprising:
   a power supply;
   a heater positioned to heat the aerosol-forming, substrate to form an aerosol;
   a controller configured to control a supply of power from the power supply to the heater; and
   a gas sensor that is sensitive to a particular gas or gases, a response of the gas sensor being dependent on a temperature of the gas sensor, and
   wherein the controller is connected to the gas sensor and is further configured to monitor signals from the gas sensor,
   wherein the gas sensor is configured to operate within an operational temperature range above ambient temperature, and
   wherein the gas sensor is positioned such that the heater is configured to heat the gas sensor to within the operational temperature range when heating the aerosol-forming substrate to form an aerosol.

2. The aerosol-generating device according to claim 1, wherein the gas sensor is a semiconductor gas sensor.

3. The aerosol-generating device according to claim 1, wherein the gas sensor is a metal-oxide gas sensor.

4. The aerosol-generating device according to claim 1, wherein the gas sensor is configured to operate between 200° C. and 400° C.

5. The aerosol-generating device according to claim 1, wherein the controller is further configured to monitor an electrical resistance or change of electrical resistance of the sensor.

6. The aerosol-generating device according to claim 1, further comprising a plurality of gas sensors, at least two of the gas sensors configured to be sensitive to different gases.

7. The aerosol-generating device according to claim 1, wherein the heater is mounted on a supporting substrate, and
   wherein the gas sensor is mounted on the supporting substrate proximate to the heater.

8. The aerosol-generating device according to claim 7, wherein the supporting substrate is configured for insertion into the aerosol-forming substrate.

9. The aerosol-generating device according to claim 7, wherein the gas sensor is disposed on the substrate overlying the heater.

10. The aerosol-generating device according to claim 7, wherein the gas sensor is disposed on an opposite face of the substrate to the heater.

11. The aerosol-generating device according to claim 7, wherein the gas sensor and the heater are disposed in a single layer on one surface of the substrate.

12. The aerosol-generating device according to claim 1, wherein the controller is further configured to stop or to reduce the supply of power to the heater based on the signals from the gas sensor.

13. The aerosol-generating device according to claim 1, wherein the aerosol-generating device is an electrically operated smoking device configured to heat a tobacco-based substrate.

14. An aerosol-generating device configured to heat an aerosol-forming substrate, comprising:
   a power supply;
   a supporting substrate;
   a heater disposed on the supporting substrate to heat the aerosol-forming substrate to form an aerosol;
   a semiconductor gas sensor that is sensitive to a particular gas or gases, and being disposed on the supporting substrate; and
   a controller configured to control a supply of power from the power supply to the heater,
   wherein the controller is connected to the gas sensor and is further configured to monitor signals from the gas sensor,
   wherein the gas sensor is configured to operate within an operational temperature range above ambient temperature, and
   wherein the gas sensor is positioned such that the heater is configured to heat the gas sensor to within the operational temperature range when heating the aerosol-forming substrate to form an aerosol.

15. The aerosol-generating device according to claim 14, wherein the aerosol-generating device is an electrically operated smoking device configured to heat a tobacco-based substrate.

16. A heating assembly for an aerosol-generating system, configured to heat an aerosol-forming substrate; the heating assembly comprising:
   a heater positioned to heat the aerosol-forming substrate to form an aerosol; and
   a gas sensor that is sensitive to a particular gas or gases, wherein a response of the gas sensor is dependent on a temperature of the gas sensor, wherein the gas sensor is configured to operate within an operational temperature range above ambient temperature, and wherein the gas sensor is positioned such that the heater is configured to heat the gas sensor to within the operational temperature range when heating the aerosol-forming substrate to form an aerosol.

* * * * *